United States Patent [19]

Phipps, Jr.

[11] Patent Number: 5,714,379
[45] Date of Patent: Feb. 3, 1998

[54] BIODEGRADATION OF VOLATILE ORGANIC CONTAMINANTS FROM AIR USING BIOLOGICALLY ACTIVATED FOAM

[75] Inventor: Donald W. Phipps, Jr., Costa Mesa, Calif.

[73] Assignee: National Water Research Inst., Fountain Valley, Calif.

[21] Appl. No.: 382,284

[22] Filed: Feb. 1, 1995

[51] Int. Cl.$^6$ .................................................. A61L 9/01
[52] U.S. Cl. ........................ 435/266; 210/601; 435/262; 435/287
[58] Field of Search ................. 435/262, 266, 435/287; 210/601

[56] References Cited

U.S. PATENT DOCUMENTS

| | | |
|---|---|---|
| 3,959,127 | 5/1976 | Bartha et al. . |
| 3,982,998 | 9/1976 | Hitzman et al. . |
| 4,211,645 | 7/1980 | Zajic et al. . |
| 4,226,939 | 10/1980 | Wegner . |
| 4,242,458 | 12/1980 | Child et al. . |
| 4,272,375 | 6/1981 | Pollock . |
| 4,530,905 | 7/1985 | Freedman . |
| 4,681,851 | 7/1987 | Baumgarten et al. . |
| 5,021,069 | 6/1991 | Whellock et al. . |
| 5,149,652 | 9/1992 | Seals et al. . |
| 5,174,378 | 12/1992 | Costerton et al. . |
| 5,190,668 | 3/1993 | Chuang . |
| 5,198,000 | 3/1993 | Grasso et al. . |
| 5,211,848 | 5/1993 | Friday et al. . |
| 5,232,596 | 8/1993 | Castaldi . |
| 5,240,598 | 8/1993 | Portier et al. . |
| 5,248,395 | 9/1993 | Rastelli et al. . |
| 5,248,587 | 9/1993 | Wong et al. . |
| 5,266,208 | 11/1993 | Stahly et al. . |
| 5,298,164 | 3/1994 | Hapach et al. . |
| 5,451,320 | 9/1995 | Wang et al. .................. 210/604 |

OTHER PUBLICATIONS

Ridgway, et al., "Identification and Catabolic Activity of Well–Derived Gasoline–Degrading Bacteria from a Contaminated Aquifer", *Applied and Environmental Microbiology*, vol. 56, No. 11, Nov. 1990, pp. 3565–3575.

*Primary Examiner*—Leslie Wong
*Attorney, Agent, or Firm*—Knobbe, Martens Olson & Bear, LLP

[57] ABSTRACT

A bioreactor is disclosed which degrades volatile organic contaminants (VOCs) from air using biologically activated foam. The reactor includes a foam generator, a reaction pipe in fluid communication with the foam generator and a defoamer in fluid communication with the reaction pipe. The reactor can also include a chemostat.

10 Claims, 6 Drawing Sheets

BIODEGRADATION OF VOLATILE ORGANIC CONTAMINANTS FROM AIR USING BIOLOGICALLY ACTIVATED FOAM

FIELD OF THE INVENTION

A bioreactor and method are described for degrading volatile organic contaminants (VOCs) present in air streams using a biologically activated foam.

BACKGROUND OF THE INVENTION

Environmental contamination by volatile organic contaminants (VOCs) released both by unintentional means and as a byproduct of industrial processes has become a major environmental issue in the latter part of this century. Deleterious long and short-term effects on humans as a result of exposure to many of these compounds have been fairly well documented. As a consequence, VOC contamination is of great interest to health and regulatory agencies, and removal of VOCs from the environment has increasingly become a national goal.

Many VOC removal schemes rely on volatilization of the contaminants, with subsequent transport from the contamination site on a stream of air. Additionally, in the case of industrial processes, VOCs can be released directly to the atmosphere. As a consequence, there is a great need to develop methods for removing VOCs from air in a cost effective manner.

Current on-site technology for the physico-chemical removal of VOCs from air includes (1) conversion to harmless products such as $CO_2$ and water by combustion, and (2) entrainment in absorptive media such as granular activated carbon (GAC). Combustion of VOCs, though commonly performed, is not cost effective unless the concentration of contaminants is relatively high. As the concentration of VOCs declines, entrainment methods such as GAC adsorption are often utilized. Entrainment methods, however, do not modify the contaminants, but instead concentrate them on a fixed medium which must then be transferred off site for further treatment.

Biological treatment methods for VOC removal from air offer many advantages over physico-chemical processes. As the concentration of VOCs falls significantly below the lean combustion limit, the efficiency of engines and catalytic combustion declines, requiring an increased cost in energy input compared to biological removal methods. In biological treatment methods, as with GAC, the contaminants are captured by a medium (a biofilm on a support). Unlike GAC, however, biological treatment methods degrade the contaminants to harmless products directly, negating the requirement for further treatment off site.

Agencies responsible for the removal of VOC contamination from the environment have therefore become increasingly interested in the development of vapor phase bioreactors (biofilters). Current state-of-the-art vapor phase bioreactors are typically containments filled with an internal packing which is colonized by VOC-degrading microorganisms, which may or may not actively interact with the VOCs. Contaminated air is introduced into the reactor, while a liquid medium containing a source of nitrogen, phosphorus, sulfur, and other inorganic trace elements necessary for microbial development is pumped over the packing. Through respiration, the resultant biofilm of organisms that develops on the packing degrades the VOC(s) of interest to $CO_2$ and water.

The processing capacity of these reactors is a function of the transport of contaminant carbon to the biofilm on the packing, which can become rate limiting when VOCs of low solubility, such as many gasoline constituents, are processed. Therefore, it is often desirable to construct vapor-phase reactors using packings with very high surface/volume ratios. This results, however, in smaller void spaces between the packing particles in order to keep the size of the reactor vessel within practical limits.

Maximal degradation of VOCs occurs in vapor phase reactors when biofilm organisms are expending energy for growth, and thus have large requirements for respiratory carbon. Large amounts of VOC carbon can be processed by these reactors under this condition. However, as biomass accumulates on the fixed packing, two basic problems develop. First, diffusion of oxygen into the biofilms can become limiting, especially with relatively soluble VOCs such as benzene and toluene. This tends to limit the efficiency of the biofilm. Second, and more importantly from an operating standpoint, accumulation of biomass and metabolic products such as extracellular polysaccharides can block the void spaces in the reactor. This is especially true when high surface area/volume packing is used. As biological material fills the void spaces, contaminated air flow follows the path of least resistance and can exclude large portions of the packing from gas exchange. This effect leads to a precipitous decline in reactor performance and necessitates cleaning the packing to remove the superfluous biomass.

Cleaning methodologies usually involve washing the packing, either while in the reactor vessel or after removal. In either case, the reactor must be taken off-line for cleaning, resulting in an overall decrease in the amount of VOCs which can be processed in a given period of time. In a worst case, biofouling can require complete removal of the packing and replacement, which is very expensive because the cost of the packing is often the major component of the reactor's construction cost.

Thus, there is a great need for a cost effective vapor phase bioreactor which utilizes a packing material having a high surface area/volume ratio; which maintains a biofilm of a controlled, uniform thinness; and which does not biofoul under conditions promoting maximal rates of VOC biodegradation.

The use of microorganisms in a foam has been described for a purpose unrelated to VOC degradation. U.S. Pat. No. 3,982,998 to Hitzman, et al., which is incorporated herein by reference, discloses a process for producing a proteinaceous food product using methanol foam fermentation by microorganisms. The methanol carbon source in Hitzman is supplied in the liquid phase.

SUMMARY OF THE INVENTION

In accordance with a first aspect of the present invention, there is provided a method of degrading volatile organic contaminants (VOCs). The method includes generating a foam by incorporating VOC-containing air into a liquid containing a surfactant, nutrients, and VOC-degrading microorganisms. The VOCs are degraded into $CO_2$ and other degradation components through metabolism by the microorganisms. The method can additionally include breaking the foam into a liquid phase, which is recovered, and a gaseous phase, which is released. The recovered liquid phase can be treated to maintain a desired level of surfactant, nutrients, and microorganisms. In addition, VOC-containing air can be incorporated into the treated liquid phase to regenerate the foam. The foregoing steps can be repeated a plurality of times or performed simultaneously.

In accordance with a second aspect of the present invention, there is provided a bioreactor for degrading VOCs. The bioreactor includes a foam generator, a reaction pipe, and a defoamer. The foam generator generates a foam by incorporating VOC-containing air into a liquid containing a surfactant, nutrients, and VOC-degrading microorganisms. The liquid can additionally contain carbon-based cofactors or co-metabolites which do not interfere with degradation of VOCs. The foam generator can include a first port for receiving the VOC-containing air, a second port for receiving the liquid containing the VOC-degrading microorganisms, and a mixer for mechanically combining the VOC-containing air with the liquid to create a biologically activated foam. In some embodiments, the liquid contains no substantial source of carbon usable as a feedstock to the microorganisms. In other embodiments, the liquid contains no substantial source of carbon. The reaction pipe is in fluid communication with the foam generator. The foam produced by the foam generator flows at a sufficiently slow rate through the reaction pipe, and the reaction pipe has a sufficient length to allow time for the microorganisms to degrade the VOCs into $CO_2$ and other degradation components. After flowing through the reaction pipe, the foam enters the defoamer, which is in fluid communication with the reaction pipe. The defoamer has an effluent port for releasing the $CO_2$ derived from the biodegraded VOCs. The defoamer can be a liquid sprayer, which mechanically disrupts the biologically activated foam.

In one embodiment, the bioreactor can additionally include a chemostat. In this embodiment, the chemostat is connected in series between the defoamer and the foam generator. The chemostat is configured to modify the liquid phase recovered from the defoamer so that the liquid phase contains appropriate amounts of surfactant, nutrients, and microorganisms. The chemostat can be configured to activate a removal pump when removal of biomass is required to maintain a physiological parameter within a desired range. The chemostat can also be configured to activate an addition pump when addition of medium is required to maintain a physiological parameter within a desired range.

In accordance with a third aspect of the present invention, there is provided a foam for degrading VOCs. The foam can be produced by mechanically combining a gaseous phase containing VOCs with a liquid phase containing nutrients and VOC-degrading microorganisms. The liquid phase can also include a surfactant. In one embodiment, the liquid phase contains no substantial source of carbon usable as a feedstock to the microorganisms.

DETAILED DESCRIPTION OF THE INVENTION

Figure 1:
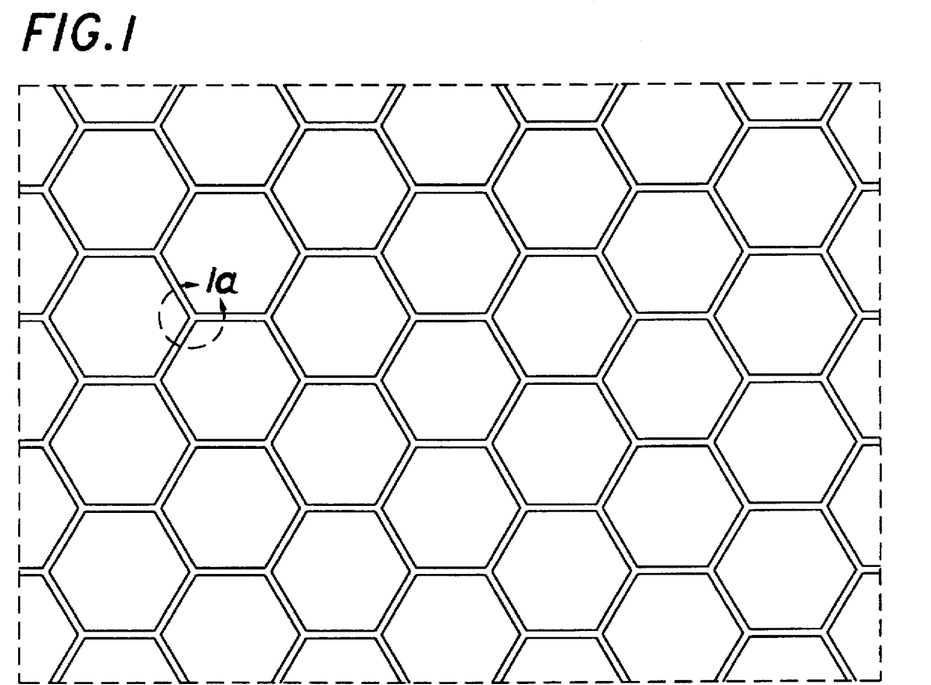
FIG. 1 is a schematic representation of a biologically activated foam according to the present invention.
Figure 1A:
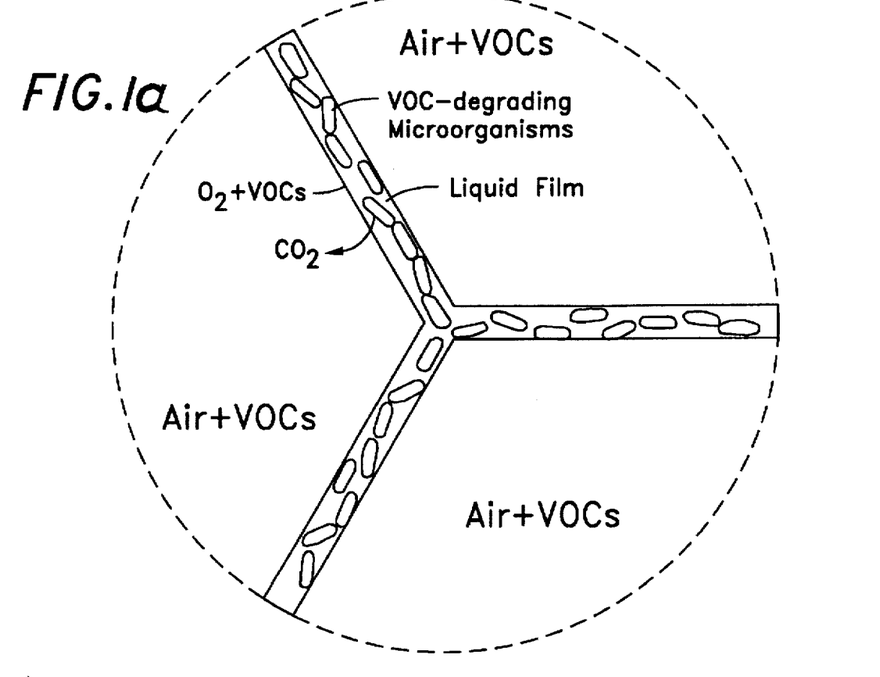
FIG. 1a is an enlarged schematic view of a segment of the biologically activated foam illustrated in FIG. 1.

In accordance with a first aspect of the present invention, there is provided a biologically activated foam for cost effective degradation of volatile organic contaminants (VOCs). The biologically activated foam of this aspect of the invention is illustrated in FIG. 1 and FIG. 1a. The foam comprises a liquid phase and a gaseous phase. The liquid phase includes one or more VOC-degrading microorganisms and nutrients therefor. Preferably, the liquid phase also includes a surfactant to enhance emulsification. The gaseous phase includes the VOCs to be degraded.

The foam is preferably semi-stable, having a bubble lifetime of greater than one minute. Preferably, the foam is composed of bubbles less than approximately 1,000 micrometers in diameter, and more preferably 100–1,000 micrometers in diameter. The approximate gas content of the foam is preferably at least 80%. The foam's high surface area/volume ratio, preferably from approximately 8,000 to 80,000 $m^2/m^3$, favors efficient mass transport, especially of lower solubility compounds. Additionally, the walls of the bubbles act as a support for the VOC-degrading microorganisms suspended therein. The resultant thin biofilm is essentially a monolayer, exposed on both sides to air. Oxygen transport is maximized in this film, eliminating diffusion limitations to the VOC-degrading organisms. As the organisms suspended within the liquid film respire, they convert the VOCs to $CO_2$, which rapidly diffuses into the gas space of the bubble.

Unlike conventional fixed-film reactor systems, gas transport through the biologically activated foam of the present invention is not adversely affected by the overproduction of organisms or their metabolic products because the active biofilm is produced and maintained at a stable thickness each time a foam bubble is formed. Thus, the present invention's emulsion of gas and liquid provides a dynamic bioreactor packing which promotes maximal degradation of VOCs.

As will be readily apparent to one having ordinary skill in the art, a variety of microorganisms can be used to degrade VOCs. The microbes selected can be adjusted for optimum degradation of the particular VOCs desired to be degraded. Microbes that can be incorporated into the liquid phase of the foam may include any VOC-degrading organisms. For example, bacteria of the genera Pseudomonas, Nocardia, Corynebacterium, and Alcaligenes can be used. The microbes can be either native or bioengineered. The microorganisms can be utilized as pure cultures or in combination as consortia.

Nutrients contained in the liquid phase of the foam include inorganic nutrients, such as nitrogen, phosphorus, and sulfur, as well as all other elements required for microbial growth on simple carbon sources. In one preferred embodiment, the liquid phase contains no substantial source of carbon. However, the liquid phase of this embodiment can contain carbon derived from microbial metabolism as well as carbon-based surfactants and vitamins, which do not interfere with degradation of the VOC carbon in the gaseous phase of the foam. In other embodiments, the liquid phase can contain carbon-based cofactors and co-metabolites which do not interfere with degradation of the VOC carbon. These cofactors or co-metabolites can aid in the degradation of VOC carbon in the gaseous phase. For instance, methane can be used as a co-metabolite in the degradation of trichloroethylene. The temperature and pH are chosen to optimize metabolism of the microbes or microbial consortia. For many VOC-degrading microbes, room temperature is preferred and pH is preferably maintained in the range of approximately 6.8–7.8. An exemplary medium formulation is presented below in Table I.

TABLE I

Formulation of HCMM2 Minimal Salts Medium

| Component | Milligrams/Liter | Millimoles/Liter |
| --- | --- | --- |
| $KH_2PO_4$ | 1360 | 10 |
| $Na_2HPO_4$ | 1420 | 10 |
| $KNO_3$ | 500 | 4.99 |
| $(NH_4)_2SO_4$ | 2380 | 18 |
| $MgSO_4 \cdot 7H_2O$ | 50 | 0.200 |
| $CaCl_2 \cdot 2H_2O$ | 10 | 0.068 |
| $H_3BO_4$ | 2.86 | 0.046 |
| $MnSO_4 \cdot H_2O$ | 1.54 | 0.0091 |
| $Fe(NH_4)_2(SO_4) \cdot 6H_2O$ | 3.53 | 0.0090 |
| $CuSO_4 \cdot H_2O$ | 0.0392 | 0.000157 |
| $ZnCl_2$ | 0.0209 | 0.000153 |
| $CoCl_2 \cdot 6H_2O$ | 0.0405 | 0.000170 |
| $Na_2MoO_4 \cdot 2H_2O$ | 0.0252 | 0.000104 |

Surfactants are chosen based on biocompatibility with the microorganisms being used. Exemplary surfactants include, but are not limited to, Triton X-100, Sodium dodecyl sulfate (SDS), Nonidet P-40, and silicon-based formulations such as DC-193. Additionally, in order to avoid inhibiting degradation of the VOCs, the surfactants preferably do not provide the organisms with a metabolizable source of carbon as determined by appropriate bioassays.

VOCs amenable to treatment using the foam include naturally occurring or xenobiotic aromatic and aliphatic compounds with vapor pressures sufficient to allow transport in the vapor phase. Exemplary compounds include gasoline hydrocarbons, trichloroethylene, ethers, and ketones of industrial importance.

Figure 2:
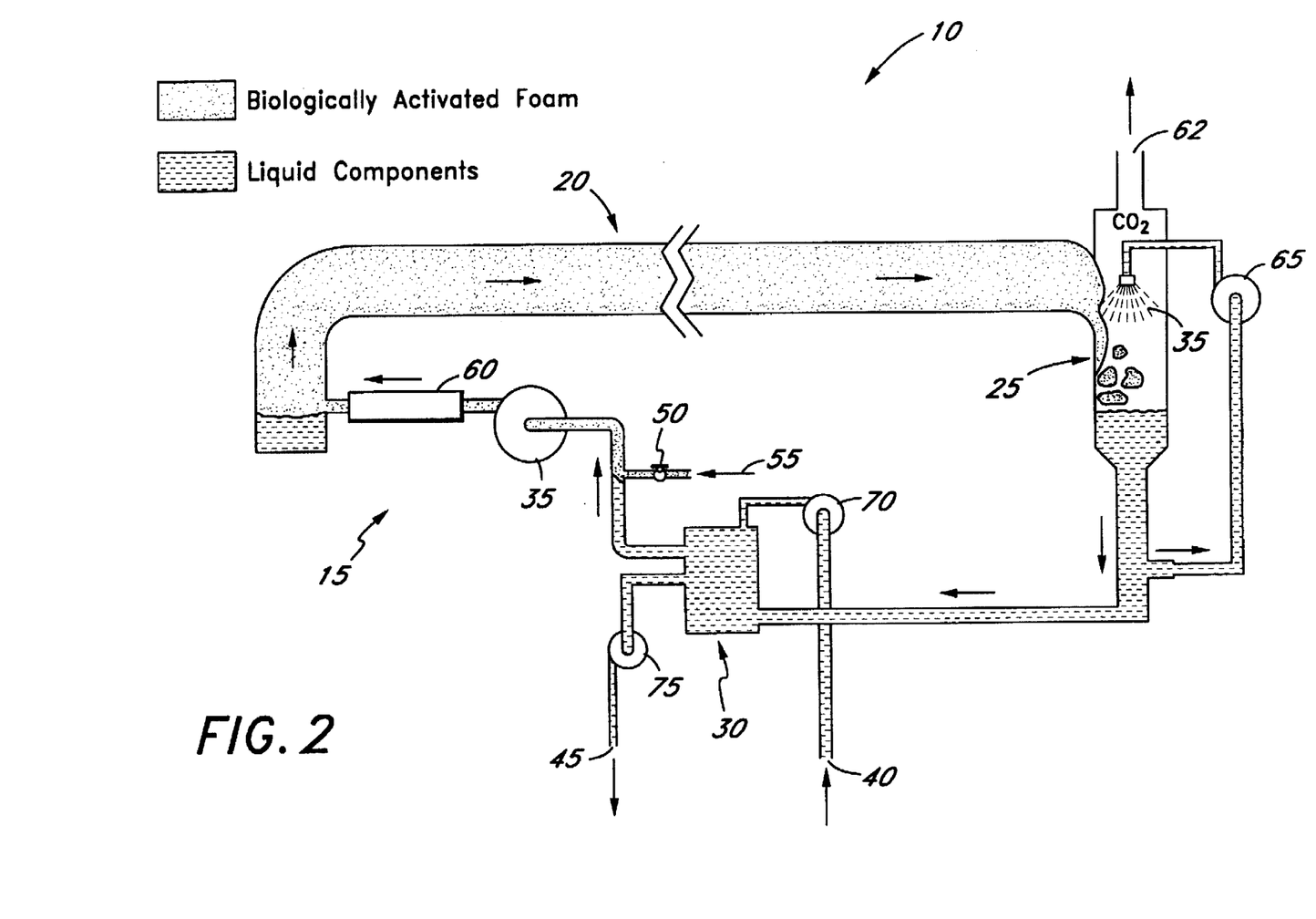
FIG. 2 is a schematic representation of a biologically activated foam reactor according to the present invention.

In accordance with a second aspect of the present invention, there is provided a bioreactor 10 and method for efficient and cost effective degradation of VOCs from air without the inherent problems of oxygen limitation and biofouling currently associated with conventional fixed-film vapor phase reactors.

Referring to FIG. 2, the bioreactor 10 preferably includes three basic system components: (a) a foam generator 15; (b) a reaction pipe 20; and (c) a defoamer 25. In a particularly preferred embodiment, the bioreactor 10 also includes a chemostat 30 configured to maintain a preferred physiological state of the biomass.

The foam generator 15 produces foam by combining VOC-containing air with a liquid based nutrient-containing medium, microorganisms and preferably a surfactant. The foam thus produced is similar to that described above in relation to the first aspect of the present invention. Commercially available devices used to generate the foam preferably allow passive introduction of the VOC-containing air, so that additional compressors are not necessary. The foam generator 15 allows for controlled introduction of the VOC-containing air. For example, the VOC-containing air can be introduced to the low pressure side of a centrifugal or gearhead fluid pump 35 where it is mechanically mixed with the liquid by the action of the pump mechanism. The VOC-containing air can also be introduced into a venturi mixing device where static mixers produce the emulsion of air and liquid.

The reaction pipe 20 is in fluid communication with the foam generator 15. Foam produced by the foam generator 15 is allowed to flow continuously into the reaction pipe 20. The dimensions of the reaction pipe 20 are chosen such that for a given rate of foam generation, the foam's incubation time in the reaction pipe 20 is sufficient to allow for a desired degree of degradation of the VOCs into $CO_2$ and other degradation components. The reaction pipe 20 can be oriented a number of ways, including horizontally or vertically. The reaction pipe 20 preferably maintains plug-flow conditions to prevent mixing of the influent and effluent foam.

After incubating in the reaction pipe 20, the foam enters the defoamer 25, which breaks the foam into its fluid and gaseous components. The foam can be disrupted by any of a number of methods well known to those of skill in the art. Preferably, defoaming does not chemically alter the resulting liquid component. Exemplary defoaming methods include thermal disruption, such as by heated wire grids or air streams; and mechanical agitation, such as by liquid spray 35 or centrifugal force. The defoamer preferably allows for complete separation of the liquid and gaseous components of the foam emulsion. Defoamed liquid is recovered from the defoamer by any of a number of well-known means, such as gravity flow, while the gaseous component is allowed to diffuse into the atmosphere, or into a collection manifold for further processing by one or more serial vapor phase reactors.

The chemostat 30 provides a means for modifying the liquid phase recovered from the defoamer 25. The chemostat is equipped with sensing devices designed to monitor parameters of physiological significance, such as pH, conductivity, microbe concentration, temperature, surfactant concentration, fluid level, and specific ion and nutrient concentrations. Preferably, the chemostat is connected in series between the defoamer and the foam generator. Defoamed liquid is introduced into the chemostat unit 25, preferably by passive means. After monitoring, the parameters can be adjusted automatically or manually to optimize metabolism of the microbes or microbial consortia. Exemplary adjustments include addition of fresh medium/ surfactant through a medium addition inlet 40 and removal of excess biomass developed as a result of microbial growth during the process through a biomass removal outlet 45.

Optimal bioreactor physiologic parameters are established either by previous bench experiments or empirically during reactor start-up. Physiologic parameters are maintained during operation of the bioreactor. For example, distilled water can be added to make up for evaporative losses, or medium can be added to replace nutrient ions taken up into biomass and fluid lost due to removal of the microbes. However, the liquid phase in the reactor is preferably maintained as closed-loop as possible.

The bioreactor is constructed from nontoxic materials unaffected by either the VOC-degrading microorganisms, or the VOCs being treated. Suitable materials include PVC plastic, epoxy-coated steel, and stainless steel. Gaskets, valves, pipes and other plumbing-related components are chosen to conform to the same requirements as the bioreactor, and materials used include PVC, stainless steel, Teflon, Viton, buna rubber, or other VOC-resistant materials.

In the specific embodiment schematically illustrated in FIG. 2, VOC-contaminated air enters the bioreactor through an air metering valve 50 at the inlet 55 of the foam generating pump. The VOC-contaminated air is combined with liquid containing microbes, nutrients, and surfactant. The resultant combination is pumped by the foam generator pump 35 into a static in-line mixer 60, where the air and liquid are entrained into a semi-stable biologically activated foam. The foam is displaced into the reaction pipe 20. As the foam continues to enter the reaction pipe 20, it is displaced along the length of the reaction pipe while incubating therein. Foam subsequently enters the defoamer 25 where a liquid spray 35 impinges on it, breaking the bubbles and releasing gaseous products such as $CO_2$ into an exhaust manifold 62. The recovered liquid phase drains by gravity to the bottom of the defoamer. Some of the recovered liquid is pumped through the spray nozzle of the defoamer by a defoaming pump 65. The majority of the recovered liquid, however, is directed into the chemostat 30 for monitoring. If necessary, the quality of the monitored liquid phase is adjusted to maintain desired physiological parameters by addition of medium or water through the addition inlet 40 or removal of biomass through the removal outlet 45. The chemostat 25 can be configured to activate an addition pump 60 or a removal pump 75 when physiological parameters so require. The liquid phase is then recycled into the foam generator and the foam generation cycle repeated. The foregoing steps can also be performed simultaneously.

EXAMPLE

A reactor was constructed from PVC plastic and operated on the laboratory bench for a period of 74 hours. The reactor had a reaction pipe foam capacity of 1.13 liters, a liquid capacity of 600 milliliters and was operated at air flow rates ranging from 100-150 milliliters per minute. The HCMM2 minimal salts medium described above in Table I was used, and the surfactant was Triton X-100 at 0.03% v/v concentration. This surfactant concentration produced a foam of approximately 70-80% gas volume without substantially inhibiting microbial growth as determined by assays using *Pseudomonas putida* in R2A medium.

VOC-laden air was produced by volatilization of contaminants in a vapor generator consisting of a four-liter glass jar ported into the bioreactor. Selected hydrocarbon contaminants were introduced by use of septum-capped serum bottles pierced with hypodermic needles of varying bores to regulate diffusion of the compounds into the atmosphere in the jar. A mass-flow meter monitored the air flow rate through the vapor generator. Typical vapor phase concentrations of contaminants produced by this procedure ranged from 100-700 micromoles of contaminant carbon per liter of air.

The concentration of VOCs in the reactor influent and effluent was monitored every two hours using an on-line gas chromatograph.

Figure 3A:
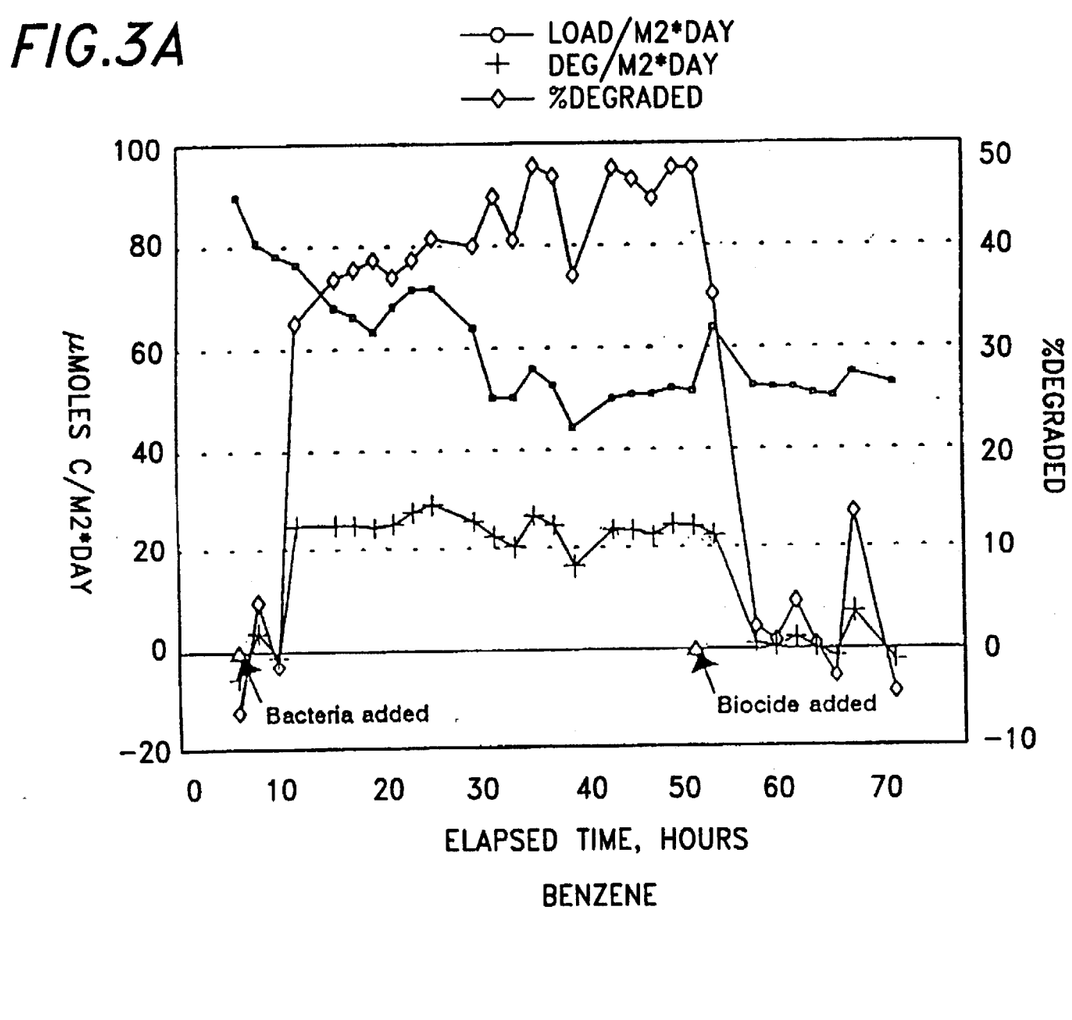
FIGS. 3A and 3B graphically depict the degradation of benzene and toluene, respectively, in a biologically activated foam reactor according to the present invention.
Figure 3B:
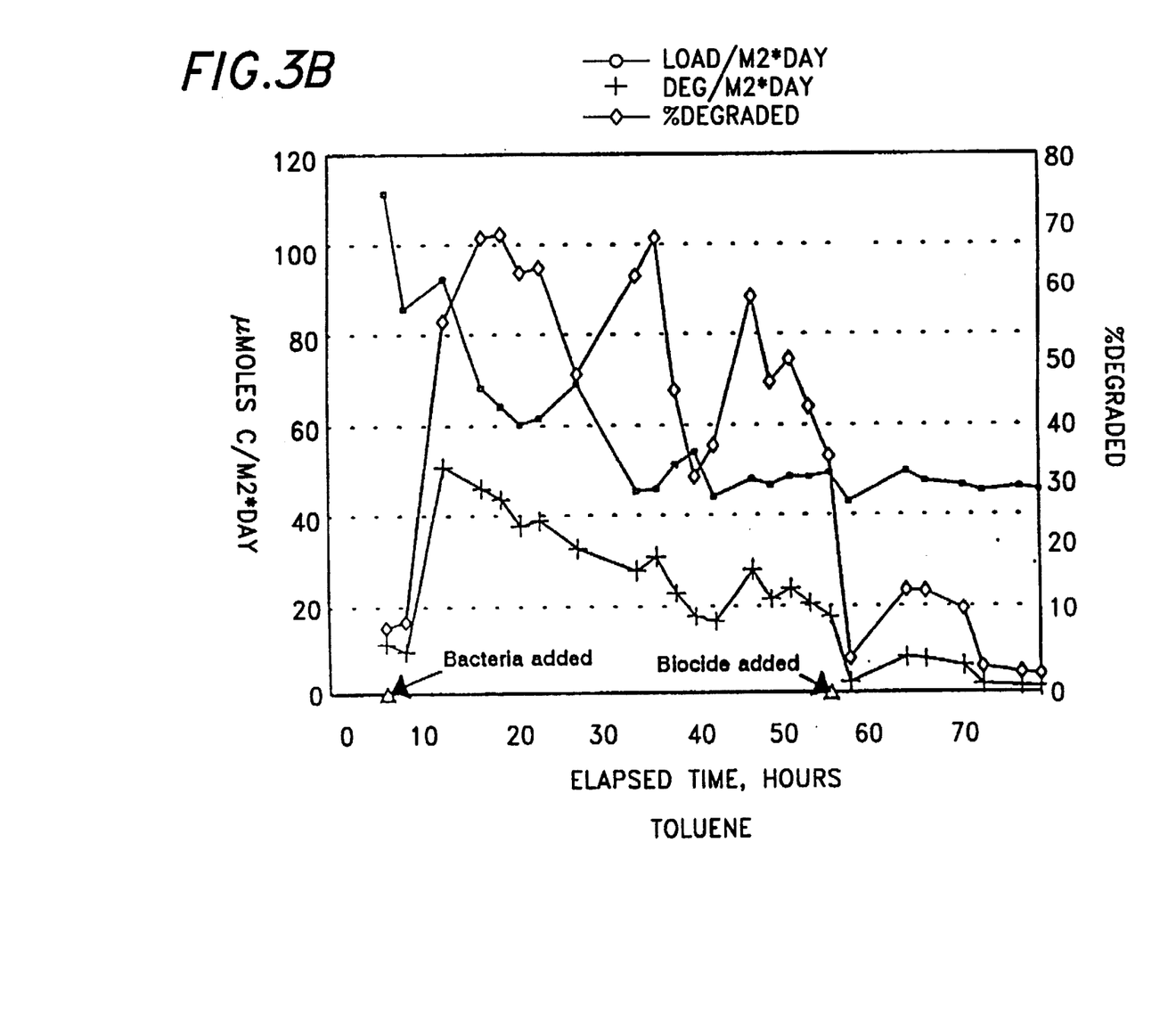

As illustrated in FIG. 3, the reactor was operated for approximately six hours before a consortium of gasoline-degrading bacteria was added. As further described in Ridgway, et al., 1990, *Appl. Environ. Microbiol.* 56 (11) :3565-3575, which is incorporated herein by reference, this consortium was initially obtained from a monitoring well sample at a gasoline contaminated site on the Seal Beach Naval Weapons Station, Seal Beach, Calif. Although members of this consortium were not specifically identified, previous studies have shown that gasoline-degrading bacteria of the genus Pseudomonas dominate the site, including *Ps. aeruginosa, Ps. putida, Ps. stutzeri, Ps. fluorescens, Ps. acidovorans, Ps. pickettii, Ps. maltophilia, Ps. alcaligenes,* and *Ps. cepacia*. Other gasoline-degrading bacteria included members of the genera Alcaligenes, Norcardia, and Micrococcus (Ridgway, et al., 1990). The consortium was subcultured in HCMM2 minimal salts medium with a mixture of hydrocarbon vapors (including benzene and toluene) as sole carbon sources, then further maintained on mixed hydrocarbon vapors in the fixed-film vapor phase bioreactor of FIGS. 4A and 4B for two years. Bacteria isolated from the resultant microbial community in the reactor were found capable of degrading a wide variety of aliphatic and aromatic compounds as sole carbon and energy sources, including both benzene and toluene.

Reactor operation continued until approximately 52 hours, at which time a biocide, isothiazolinone (Nalco 2593), was introduced. Data were collected beyond 70 hours. Reactor operating parameters were optimized manually at the beginning of the experiment, but were not adjusted later (i.e., no on-line chemostat was used).

As illustrated by FIG. 3, both benzene and toluene were degraded by the consortium present in the biologically activated foam. Degradation was not observed until the addition of bacteria, and then rapidly increased as the biota developed in the reactor. The reactor was able to degrade 41.5±4.84 percent of the benzene loaded and 49.5±16.8 percent of the toluene loaded under the conditions of the experiment. Addition of the biocide at 52 hours led to a rapid deterioration in reactor performance, indicating that degradation was mediated by the microbial population.

Figure 4A:
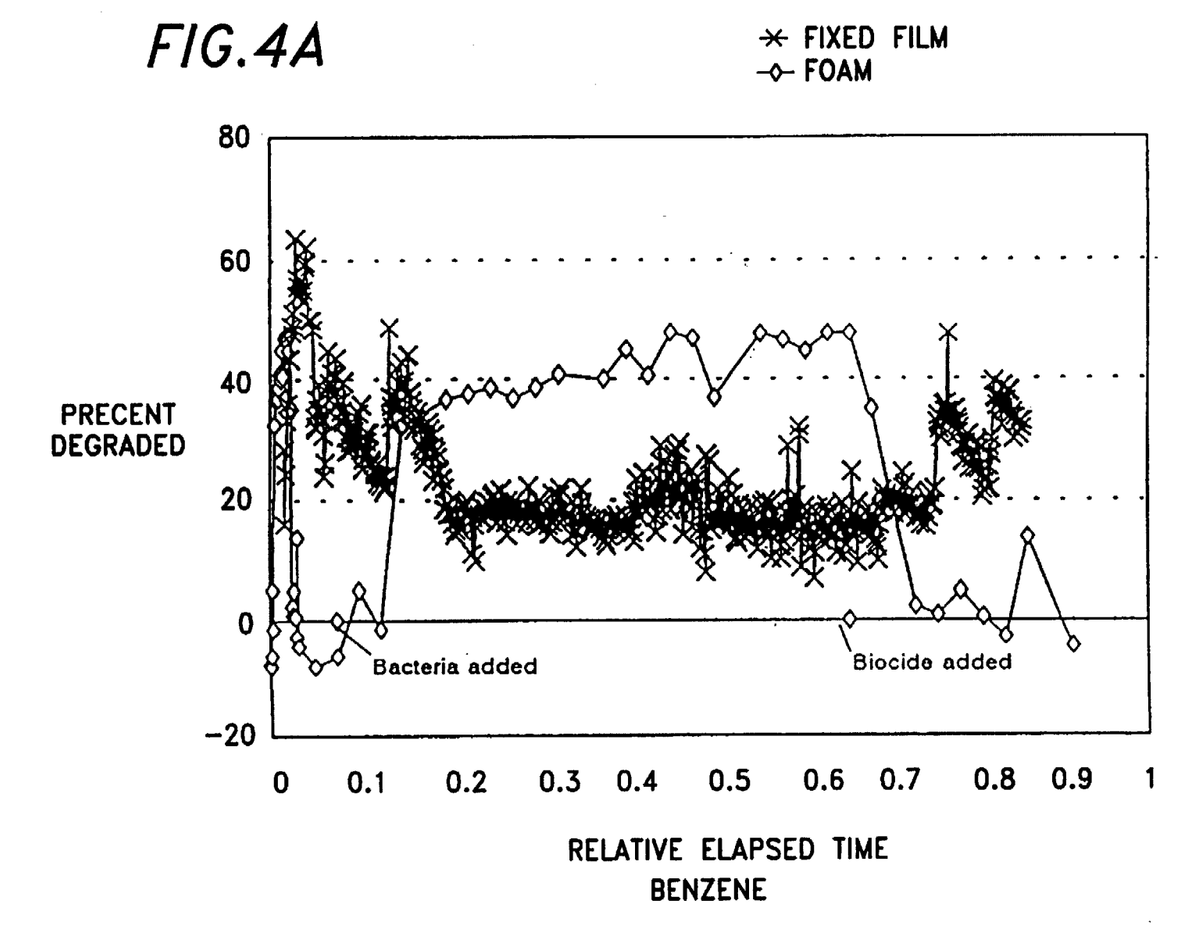
FIGS. 4A and 4B graphically depict the percentage of degradation of benzene and toluene, respectively, in a biologically activated foam reactor according to the present invention compared to that of a conventional fixed-film reactor.
Figure 4B:
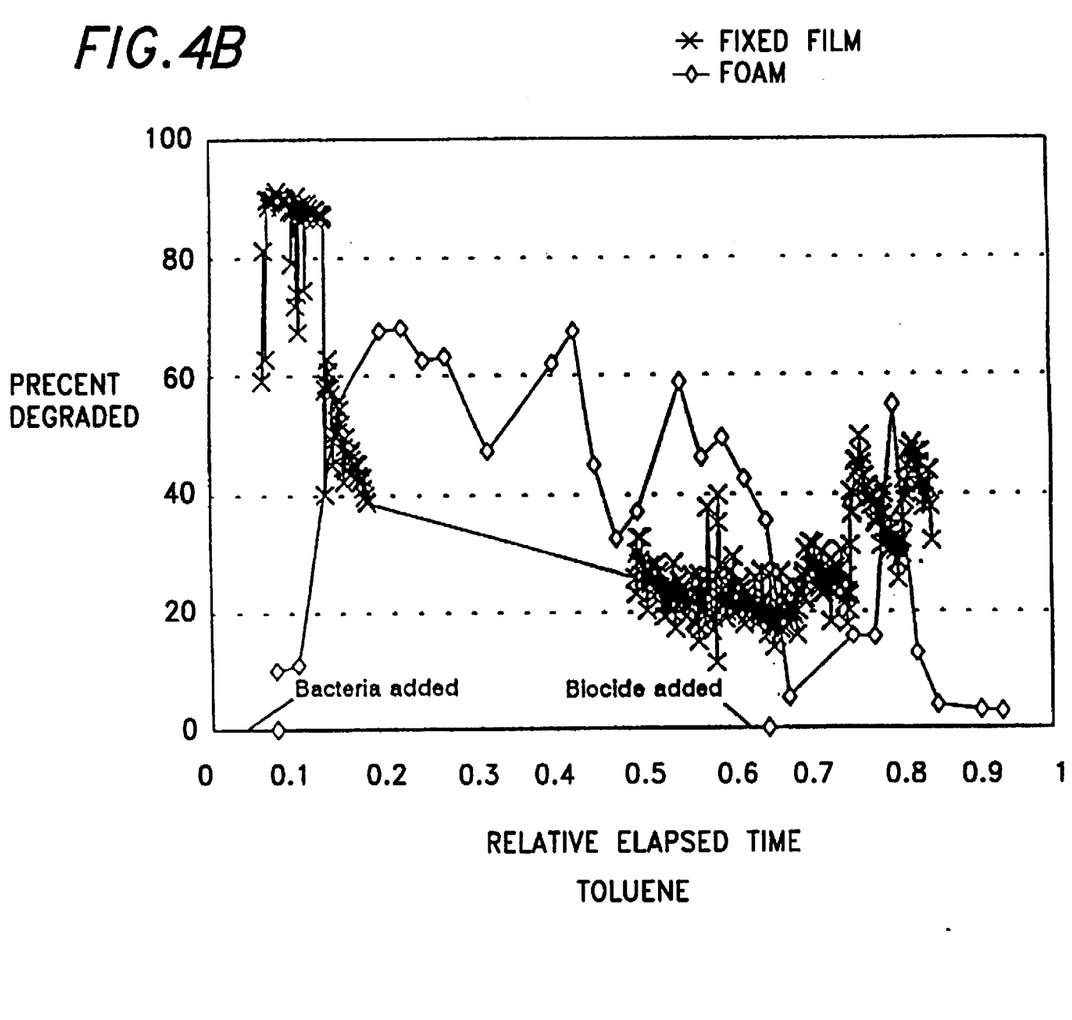

FIG. 4 illustrates the performance of the activated foam reactor of the present invention compared to a conventional fixed-film vapor phase reactor operating under similar conditions. As shown in FIG. 4, at many sample points the percentage of benzene and toluene degradation by the activated foam reactor of the present invention was over twice that of a conventional fixed-film vapor phase reactor.

Although this invention has been described in terms of certain embodiments, these embodiments are set forth for illustrative purposes, and are not intended to limit the scope of the invention. It will be apparent to those skilled in the art that various other modifications can be made to these embodiments without departing from the scope of the invention, which is properly determined upon reference to the following claims.

What is claimed is:

1. A method of degrading volatile organic contaminants (VOCs), comprising:

(a) generating a foam by combining VOC-containing air with a liquid containing a surfactant, nutrients, and VOC-degrading microorganisms, wherein the foam generated has an approximate gas content of at least 70%; and (b) degrading the VOCs into $CO_2$ and other degradation components through metabolism thereof by said microorganisms.

2. The method of claim 1, additionally comprising:

(c) breaking the foam into a liquid phase and a gaseous phase, said gaseous phase containing the $CO_2$;

(d) releasing the gaseous phase; and (e) recovering the liquid phase.

3. The method of claim 2, additionally comprising:

(f) treating the liquid phase to maintain a desired level of surfactant, nutrients, and microorganisms; and (g) combining VOC-containing air with the treated liquid phase to regenerate the foam.

4. The method of claim 3, additionally comprising repeating steps (b) through (g) a plurality of times.

5. The method of claim 3, wherein steps (b) through (g) are performed simultaneously.

6. The method of claim 1, wherein the foam generated has an approximate gas content of at least 80%.

7. A foam for degrading volatile organic contaminants (VOCs), said foam comprising:

a liquid phase containing nutrients and VOC-degrading microorganisms, said liquid phase containing no substantial source of carbon usable as a feedstock to said microorganisms; and a gaseous phase containing VOCs, wherein the foam generated has an approximate gas content of at least 70%.

8. The foam of claim 7, wherein the liquid phase further comprises a surfactant.

9. The foam of claim 7, wherein said foam is produced by mechanically combining said liquid phase with said gaseous phase.

10. The foam of claim 7, whereto the foam generated has an approximate gas content of at least 80%.

* * * * *